US010002750B2

(12) United States Patent
Toutoungi et al.

(10) Patent No.: US 10,002,750 B2
(45) Date of Patent: Jun. 19, 2018

(54) FIELD ASYMMETRIC ION MOBILITY SPECTROMETRY FILTER

(71) Applicant: Owlstone Medical Limited, Cambridge (GB)

(72) Inventors: Danielle Toutoungi, Cambridge (GB); Matthew Hart, London (GB); John Somerville, Hertfordshire (GB); Jon Pearson, Cambridge (GB); Max Allsworth, Essex (GB); Richard Orrell, Cambridgeshire (GB); Antoni Negri, Longstanton (GB); Jeremy Spinks, Cambridge (GB); Martin Holden, East Hendred (GB); Andrew H. Koehl, Cambridge (GB); Alastair Taylor, Bury St Edmunds (GB)

(73) Assignee: Owlstone Medical Limited, Cambridge (GB)

( * ) Notice: Subject to any disclaimer, the term of this patent is extended or adjusted under 35 U.S.C. 154(b) by 0 days. days.

(21) Appl. No.: 15/152,290

(22) Filed: May 11, 2016

(65) Prior Publication Data

US 2016/0336159 A1 Nov. 17, 2016

Related U.S. Application Data

(63) Continuation of application No. 14/369,121, filed as application No. PCT/IB2013/000404 on Jan. 3, 2013, now Pat. No. 9,362,099.

(60) Provisional application No. 61/583,303, filed on Jan. 5, 2012.

(51) Int. Cl.
*G01N 27/62* (2006.01)
*H01J 49/06* (2006.01)
*H01J 49/00* (2006.01)

(52) U.S. Cl.
CPC .......... *H01J 49/061* (2013.01); *G01N 27/624* (2013.01); *H01J 49/0018* (2013.01); *H01J 49/068* (2013.01); *Y10T 29/49147* (2015.01); *Y10T 29/49149* (2015.01)

(58) Field of Classification Search
CPC ..... H01J 49/061; H01J 49/068; G01N 27/624
See application file for complete search history.

(56) References Cited

U.S. PATENT DOCUMENTS

| 7,714,278 | B2 | 5/2010 | Boyle | |
|---|---|---|---|---|
| 2001/0042826 | A1* | 11/2001 | Chutjian | H01J 49/0018 250/283 |
| 2008/0054174 | A1* | 3/2008 | Boyle | G01N 27/624 250/286 |
| 2008/0191132 | A1* | 8/2008 | Boyle | G01N 27/624 250/287 |

(Continued)

FOREIGN PATENT DOCUMENTS

WO 9963579 12/1999

OTHER PUBLICATIONS

International Application No. PCT/IB2013/000404, International Search Report and Written Opinion dated Jun. 12, 2013.

*Primary Examiner* — Eliza Osenbaugh-Stewar
(74) *Attorney, Agent, or Firm* — Sheppard, Mullin, Richter & Hampton LLP

(57) ABSTRACT

Ion filter for FAIMS fabricated using the LIGA technique. The ion filter is manufactured using a metal layer to form the ion channels and an insulating support layer to hold the structure rigidly together after separation of the metal layer into two electrodes.

20 Claims, 7 Drawing Sheets

(56) References Cited

U.S. PATENT DOCUMENTS

2010/0148051 A1* 6/2010 Hart ................ G01N 27/622
  250/281
2011/0036973 A1  2/2011 Alonso

* cited by examiner

FIELD ASYMMETRIC ION MOBILITY SPECTROMETRY FILTER

CROSS REFERENCE TO RELATED APPLICATIONS

This application is a Continuation of U.S. patent application Ser. No. 14/369,121 filed on Jun. 26, 2014, which is a National Phase (371) Application of PCT Application No. PCT/IB2013/000404 filed on. Jan. 3, 2013 which claims priority to U.S. Patent Application Ser. No. 61/583,303 filed on Jan. 5, 2012, all of which are incorporated herein by reference in their entirety.

FIELD OF THE INVENTION

The present invention relates to devices and methods for ion mobility systems. More specifically, the invention relates to a filter for use with an ion mobility system.

BACKGROUND OF THE INVENTION

Mass spectrometry (MS) is an exceptionally powerful tool for chemical analysis. However, separating ions by mass will not always provide a unique signature, thus there is an ongoing demand for complementary orthogonal chemical separation methods that can be used in series with MS to aid in analysing complex mixtures.

High Pressure Liquid Chromatography (HPLC) is a technique which separates chemical mixtures based upon their physical shape and chemical functionality in solution. HPLC is often used in combination with electro-spray ionisation to pre-separate ions for further analysis via MS creating a technique known as liquid chromatography mass spectrometry (LCMS). However, even such complex techniques as LCMS cannot always uniquely identify elements in complex mixtures.

Field asymmetric ion mobility spectrometry (FAIMS) separates gaseous ions based upon their physical shape and chemical functionality in the gas phase and has previously been used as a pre-separator for MS. However, previous FAIMS systems designed for interfacing to mass spectrometers have been large, cumbersome and expensive. Such systems have also been unable to apply the highest FAIMS electric fields due to their large ion channel widths, and have also been poorly configured to couple ions effectively from the output of the FAIMS device to the MS. In addition, prior art FAIMS MS systems have been relatively slow when ideally the FAIMS device should carry out the separation on timescales commensurate with typical mass spectrometry experiments (for example, full sweeps within the duration of typical LC peaks which could be down to 1 second long, or able to step compensation voltages (CVs) to different points fast enough for Multiple Reaction Monitoring (MRM) type experiments where different ions are targeted by the mass spectrometer in sequence, with potentially up to approximately 500 ions per second being examined).

Additionally, since it is desirable for a FAIMS device to fit between the ionization source and the inlet to the mass spectrometer, it should be small and movable. Additionally, a FAIMS filter downstream of an electro spray ionization source should be configured such that it can be easily cleaned or replaced (minimizing system down time) such as when it becomes contaminated with electrospray residue which tends to occur downstream of an electrospray ionization source.

SUMMARY OF THE INVENTION

The purpose and advantages of the invention will be set forth in and apparent from the description that follows. Additional advantages of the invention will be realized and attained by the devices, systems and methods particularly pointed out in the written description and claims hereof, as well as from the appended drawings.

To achieve these and other advantages and in accordance with the purpose of the invention, as embodied, the invention includes, in one aspect, an ion filter including at least one metal electrode layer and at least one ion channel formed through the at least one electrode layer. Further included is at least one support layer adjacent the at least one electrode layer. The at least one support layer is preferably configured to maintain regions of the at least one electrode layer in fixed relative positions. The at least one support layer preferably includes an aperture formed therein configured to permit gas to flow therethrough. In accordance with illustrative embodiments, the at least one support layer formed by molding a polymer structure onto the at least one electrode layer. Additionally, the at least one support layer may be configured as an electronic circuit carrier and may include at least one capacitance in parallel with the at least one metal electrode layer. Preferably the at least one capacitance is at least partially formed by one or more discrete capacitors. The at least one support layer may include a support layer disposed on a front surface portion of the at least one electrode layer and a support layer disposed on a back surface portion of the at least one electrode layer.

The at least one support layer may be configured to provide electrical interconnection between the at least one electrode layer and ion filter drive electronics wherein the electrical interconnection is provided by wire bonding. Alternatively, the electrical interconnection may be provided via soldering. The at least one support layer may include ceramic material or a composite containing one or more of ceramic, glass and hydrocarbon materials, or it may include glass material.

The at least one support layer may further provide conductive pads for mechanical and electrical connection to the electrode layer wherein the at least one support layer is configured to provide electrical interconnection between the at least one electrode layer and the ion filter drive electronics. Additionally, the at least one electrode layer may attach to the at least one support layer by one of soldering, brazing, welding, thermocompression bonding, or via an adhesive.

In other illustrative embodiments, the at least one support layer has an expansion co-efficient approximately equal to the expansion co-efficient of the at least one electrode layer and/or is fabricated via a molding process wherein the molding process includes plating metal into a mold.

The at least one electrode layer may have a surface portion coated with a chemically inert layer wherein the chemically inert layer is Gold (Au) or is substantially formed from one or more of Nickel (Ni), Copper (Cu) and Gold (Au) wherein a mold used in the molding process is formed using a lithographic process. The lithographic process may include using ultraviolet light or x-rays. The at least one electrode layer may be plated onto the at least one support layer. The at least one electrode layer may further include at least one separating structure for maintaining a fixed mechanical separation between regions of the at least one electrode layer during a fabrication process wherein the at least one separating structure is at least partially removed during the fabrication process and wherein the removal of the separating structure provides electrical isolation between regions of the at least one electrode layer.

The at least one ion channel may form one or more serpentine slots extending through the at least one electrode layer, one or more substantially linear slots extending through the at least one electrode layer, or one or more curved slots extending through the at least one electrode layer.

In a further aspect, a system for filtering ions preferably includes a controller and an ion filter device. The ion filter device may include at least one metal electrode layer, at least one ion channel formed through the at least one electrode layer. At least one support layer is provided adjacent the at least one electrode layer and is configured to maintain regions of the at least one electrode layer in fixed relative positions. The at least one support layer includes an aperture formed therein configured to permit gas to flow therethrough. One or more apertures may be provided in proximity to the ion filter device configured to restrict the gas flow to a specified region of the ion filter device. Further provided may be a mechanism that permits interchange of the one or more apertures for selecting a region of the ion filter device through which gas flows or a mechanism for varying the dimensions of the one or more apertures to adjust the size of the region of the ion filter device through which gas flows. The controller may include an asymmetric waveform generator employing a de-tuned class E amplifier circuit configured to produce an asymmetric waveform wherein the asymmetric waveform generator further includes a Field Effect Transistor (FET) connected to a primary winding of a transformer having two secondary windings configured to deliver two waveforms of opposite polarity for providing a waveform voltage gain. The amplifier circuit may be tuned by changing the values of one or more capacitors provided in the amplifier circuit, each being composed of one or more discrete capacitors wherein a first capacitor is parallel to the electrode layer electrodes and a second capacitor is provided across the drain and source terminals of a FET. A transmission path may be provided tuned to provide a waveform to the ion filter device where the waveform properties are insensitive to changes in the position or surroundings of the transmission path wherein the transmission path is maintained at a non-zero bias voltage for delivering a bias voltage to the ion filter device and/or is mechanically flexible sufficient to enable repositioning of the ion filter device.

An electrically insulating spacer may be provided that is configured to thermally connect one or more transistors in the amplifier to a thermal heat sink whereby the spacer has a thickness appropriate to reduce capacitive coupling between transistor terminals and the heat sink. A conductive manifold cover may be provided configured to cover the system for filtering ions, including at least one aperture for accommodating transmission of gasses, and power and control signals.

It is to be understood the ion filter device may be user replaceable wherein the ion filter device is received by a receptacle having spring loaded contacts configured for providing electrical coupling between the ion filter and other portions of the system for filtering ions.

In a still further aspect of the invention in accordance with illustrative embodiments, a method for fabricating ion filter devices is provided that includes fabricating an array of support structures on a sheet, fabricating a plurality of electrode structures and attaching the electrode structures to the sheet having an array of support structures. A portion of each electrode structure is removed to provide electrical isolation between electrode pairs and the support structures. The attached electrode pairs are separated to provide individual ion filter devices. The array of support structures may be configured as a printed circuit board panel. Attaching the electrode structures to the sheet may include using soldering, brazing, welding, thermocompression bonding or adhesive bonding. Additionally, the plurality of electrode structures may be joined together in a sheet prior to their attachment to the support structures.

BRIEF DESCRIPTION OF THE DRAWINGS

The accompanying appendices and/or drawings illustrate various non-limiting, example, inventive aspects in accordance with the present disclosure.

DESCRIPTION OF THE INVENTION

Figure 1A:
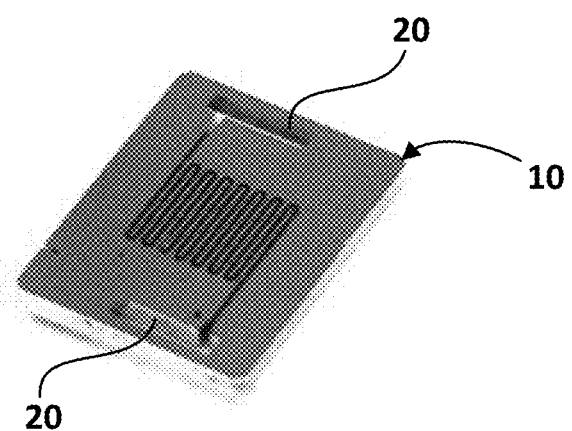
FIGS. 1A-1E depict a fabrication process in accordance with certain illustrated embodiments.

The present invention is now described more fully with reference to the accompanying drawings, in which an illustrated embodiment of the present invention is shown wherein like reference numerals depict like elements. Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

With regards to the present invention, it generally comprises a novel FAIMS filter for use in analysis of gaseous ions which is well suited for (without limitation) prefiltering and pre-separating ions for MS. The invention relates to a miniaturised low-cost FAIMS filter enabling a FAIMS system to be readily fixed and removed from the MS, and is configured to both efficiently capture ions from an electrospray device and to efficiently transfer the output of the FAIMS Channel to the inlet of a MS.

The reduced size also enables a greatly reduced residence time and smaller gap in the FAIMS ion channel enabling faster scanning at greater fields than previous approaches, thus being better suited to use in combination with LC and during MRM type experiments.

The invention also relates to a low-cost module that can be easily removed for cleaning (e.g. by sonication in solvent) or replaced by a user. Different chip designs can be provided that are optimized for different applications, and the removable design enables it to be readily changed by a user.

In accordance with an illustrated embodiment, the dimensions of the device chosen to achieve sufficient transmission of ions of interest while also providing a high degree of separation consist of a device with a thickness (channel length) of approximately 0.7 mm, FAIMS analytical gap of approximately 0.1 mm and an open area of approximately 1-50 $mm^2$ (it is not to be understood to be limited to these dimensions). It is noted, such dimensions lead to ion residence times of the order of 100 us. It is to be appreciated that such small residence times typically only produce useful separation if the separation fields are in the ultra-high range (i.e. greater than approximately 40 kV/cm) whereby only devices with an analytical gap dimensioned in accordance with this invention can sustain electric fields of this magnitude (typically at pressures of approximately one atmosphere) without breaking down. Additionally, to avoid high transmission losses with such high electric fields, a frequency of operation greater than approximately 10 MHz is preferably utilized. At such voltages and frequencies, and in order to generate the asymmetric waveforms required, a structure with a low and repeatable capacitance is preferred.

Typically in the ionization source, and immediately in front of the inlet of the mass spectrometer, there are hot gases (in the region of approximately 150-400 degrees C., depending on model of MS) and heated components that help enable formation of ions from a liquid spray and improve sensitivity of the mass spectrometer. Preferably this is the region in which the FAIMS filter chip is located, so in order to allow operation of the ionization source without compromising its performance, the FAIMS device typically needs to be able to withstand temperatures up to at least 150 C, preferably up to 250 C or more.

To make the chip module low-cost and easily replaceable and protect the drive electronics from temperatures present at the MS inlet, it is preferably to physically separate the chip from the electronics that generate the FAIMS waveforms. However, this creates an extended distance for the FAIMS drive voltages to be transmitted and it is preferably that the transmission line that brings the waveforms to the chip has a suitable impedance. It is to be appreciated the DF feeder structure is an embodiment of such a transmission line with suitable properties.

Microchip

It is to be appreciated microfabricated FAIMS filter devices having multiple, interdigitated, high-aspect-ratio, conductive fingers have a number of performance advantages over conventional macroscopic FAIMS filters. For instance, these benefits include the ability to generate extremely high electric fields for ion separation, fast ion separation times, and form-factors that are convenient for coupling of filtered ions into various types of ion detectors.

According to the prior art (see, for instance U.S. Pat. No. 7,714,278) known FAIMS filters are fabricated by forming the conductive fingers on a doped silicon wafer using a Deep Reactive Ion Etching (DRIE) technique. This technique forms high-aspect-ratio (e.g. 7:1 or greater), vertical-sided trenches (ion channels) through the full thickness of a silicon wafer, leaving a set of inter-digitated finger structures between the etched trenches. These electrically-conductive fingers serve as electrodes for establishing ion separation fields within the ion channels. To enable proper operation of the device it is important that the electric field in the ion channels is spatially uniform, that is, the variation in electric field strength and direction is as small as possible over the volume of the ion channels. This is typically achieved by ensuring that the ion channels have a high aspect ratio, and flat and parallel sidewalls. High aspect ratio is needed to reduce the effect of fringing fields at the channel entrance and exit. Flat, parallel sidewalls are needed to maintain the electric field uniform within the whole volume of the channel. It is noted actual devices have deviations from the aforesaid ideal, leading to some field non-uniformity and consequent loss in ion separation performance.

It is further noted that fabrication of FAIMS filters using DRIE on a silicon wafer (as in the cited prior art references) has a number of advantages. First, it allows relatively flat and extremely parallel ion channel walls to be formed. Second, it is a wafer-based process, meaning that many FAIMS-filter devices may be formed simultaneously on a wafer in parallel, leading to low production cost in high-volume fabrication. Third, since the ion channel structures are formed using high-resolution lithography techniques, channel dimensions can be very small (micron scales and upward) and very precisely controlled, allowing very high separation fields to be achieved.

However, these prior art fabrication methods also have a number of drawbacks. First, the fabrication processes are best suited to high-volume production, having significant setup costs and only achieving high device yield when running multiple wafers through the production process. The cost of manufacturing such devices may be very small in production volumes, for example, of ten thousand units but relatively high in production volumes of one thousand units or below. Second, etching high-quality, high-aspect-ratio trenches through the whole thickness of a silicon wafer (which may be several hundred microns thick) is technically challenging and requires highly specialized (costly) equipment and highly skilled operators. Where ion channels on the order of 100 microns width are required (implying wafer thicknesses of at least 700 microns to maintain a high aspect ratio) it may become very difficult to etch a uniform trench through the required thickness of silicon using the DRIE technique. Third, silicon is not an ideal conductive material and must be doped with atoms of other elements (e.g. boron, phosphorus) to become highly conductive, adding manufacturing cost and complexity. Silicon also forms a native insulating oxide on its surface. Although thin, such oxide layers can inhibit cancellation of ion charges on the sidewalls of the ion channels, impairing the performance of the FAIMS filter (this can be particularly problematic at the higher temperatures often encountered in MS inlet). They can also act as sites for accumulation of charges on the surface of the device, creating uncontrolled electric field components within the ion channels.

Fabrication Using LIGA Technique

Thus, there is a need for FAIMS filter devices that do not suffer from these drawbacks. Such devices should ideally be inexpensive to produce (even in small volumes), have highly parallel ion channels that are on the order of 100 microns wide and 700 microns long, and be fabricated from conductive materials that are able to effectively carry away charge from ions that collide with the filter surfaces, even after prolonged operation at high temperatures.

In accordance with an illustrated embodiment, these needs can be met by FAIMS filter devices manufactured using a metal layer to form the ion channels and an insulating support layer to hold the structure rigidly together after separation of the metal layer into two or more electrodes. One method for forming the ion channels in metal is to use a microfabrication technique known as LIGA— Lithographie, Galvanoformung, Abformung, which generally is technology used to create high-aspect-ratio microstructures (see, for example "Fundamentals of Microfabrication", Madou, CRC Press). As one skilled in the art would understand, LIGA consists of three main processing steps; lithography, electroplating and molding. There are two main LIGA-fabrication technologies, X-Ray LIGA, which uses X-rays produced by asynchrotron to create high-aspect ratio structures, and UV LIGA, a more accessible method which uses ultraviolet light to create structures with relatively low aspect ratios.

The LIGA method can be utilized to produce high-aspect-ratio structures by electro-plating onto a conductive substrate onto which a mould has been deposited. This mould is normally formed using a photo-resist that is spun onto the conductive substrate, exposed to a light pattern that defines the mould structure then developed to remove photo-resist that is the negative of the structure to be formed by plating. Metal is then plated into the mould in a plating bath. After plating, the photo-resist is removed and the plated material released from the conductive substrate—producing a metal structure in the form required. To achieve high-aspect-ratio vertical sidewalls in the mould structure, the photo-resist can be exposed using an x-ray source or, preferably if low-cost fabrication is required, an ultra-violet light source (in a technique known as UV-LIGA). In the UV-LIGA technique, the mould is often formed using a commercially available photo-resist, such as, SU-8 (Microchem, Newton, Mass.) which is suitable for producing high-aspect ratio moulds.

Figure 1B:
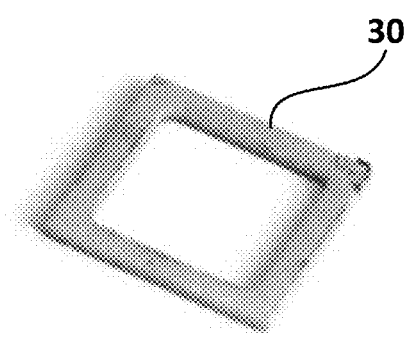
Figure 1C:
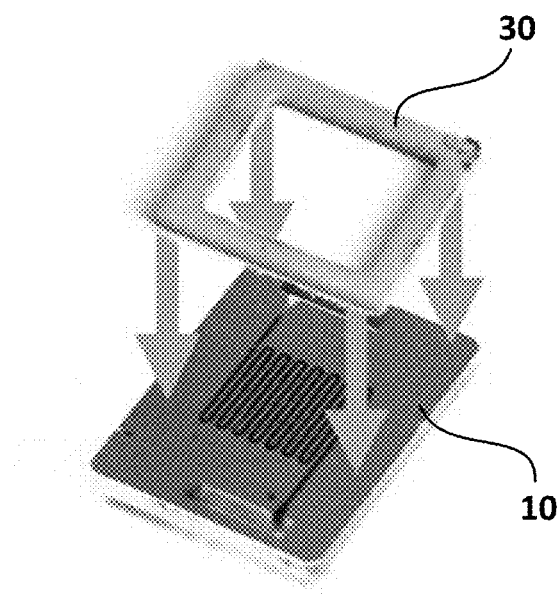
Figure 1D:
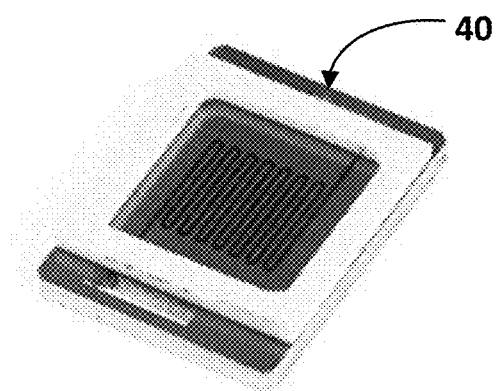

The high-level process for producing a micro-fabricated FAIMS device using a LIGA process is preferably as follows: the interdigitated high-aspect ratio finger structures are produced by plating a metal into a mould (as described above), conducting any finishing required such as lapping or polishing to the required thickness, and then releasing the metal structure from the mould. The resulting structure produced is a metal sheet having a serpentine trench or slot running through it, which separates the fingers by a precisely defined distance. In an exemplary implementation, this distance is preferably 100 microns and the sheet is preferably 700 microns thick. With reference now to FIG. 1A, at this stage, the slot does not extend directly to the edges of the metal sheet 10 but instead stops proximal of the sheet edges, thus leaving small tabs 20 of metal that hold the sheet together in one piece. A typical example is shown in FIG. 1A having a metal ion channel layer. In a separate process, an electrically insulating support structure (frame) is made, to which the metal sheet will later be attached. This support structure preferably has a through-hole positioned adjacent to the ion channels formed in the metal to permit gas to flow through it. An example of such a support structure (insulating frame 30) is shown in FIG. 1B. Once the slotted metal piece 10 and the support structure (insulating frame 30) have been formed, they are bonded together (see for instance FIG. 1C) to form a two-layer laminated structure 40 as shown in FIG. 1D. Finally, after bonding to the support 30, the tabs 20 that hold the metal sheet 10 together at the edges are cut, separating the metal into two halves that are both mechanically fixed to the support 30, but electrically isolated from one another to provide a finished FAIMS filter 60, see for instance FIG. 1E.

Illustrative Implementations for the Metal Layer

As described above, the metal layer 10 that forms the ion channels can be made using either conventional X-ray LIGA or by UV-LIGA techniques. The metal used to form the structure might typically be nickel, either relatively pure nickel or hardened nickel that has been modified by the addition of other elements. Other metals could also be used to form the plated structure and could be chosen according to criteria including ease of plating, material cost, thermal characteristics, magnetic properties, electrical properties, mechanical properties and chemical properties.

To allow electrical contacts to be made upon the structure (for application of FAIMS drive and tuning signals) it is advantageous to coat the metal structure with another metal, typically by electro-plating. Such coatings may also be used to improve the chemical inertness of the ion channels and to facilitate attachment to the support structure. As an example, a nickel structure might be modified by over-plating with a thin (e.g. 1 micron) coating of gold to facilitate certain types of electrical connection (for example gold thermo-compression wire bonding or gold-tin eutectic soldering) and/or to reduce the possibility of unwanted chemical reactions between the gas flow and the FAIMS filter (for example oxidation of the filter surface). Reducing surface oxidation will reduce the likelihood of charge accumulation on the filter surfaces, improving the performance of the device.

Illustrative Embodiments of the Insulating Support Layer

Figure 1E:
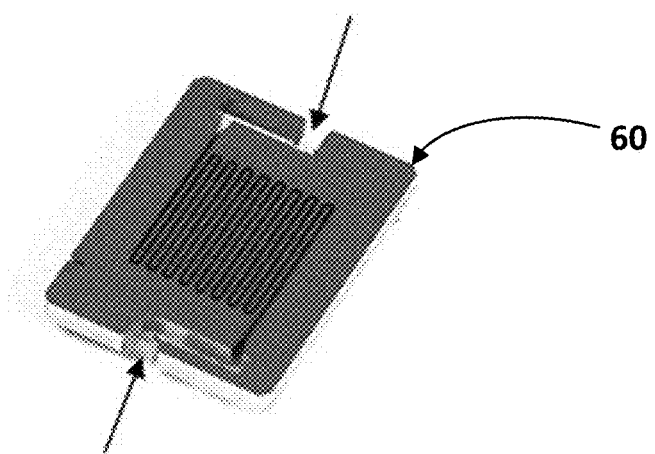

It is to be appreciated a primary function of the support layer is to provide an electrically insulating rigid mechanical support to which the metal layer 10 is attached prior to removal of the metal tabs 20 holding that layer in one piece. Removal of the tabs separates the metal layer mechanically and electrically into at least two pieces (FIG. 1E). The bonded support layer serves to maintain the relative position of these two pieces ensuring that the width of the ion channels remains constant after separation.

Since the laminated FAIMS device may be required to operate over a range of temperatures and because bonding of the support may occur at a temperature other than the operating temperature, it is desirable that the thermal expansion coefficients of the metal layer and support are at least reasonably well matched. It is noted operation of the FAIMS device requires high-electric fields be established between at least two separated electrodes formed in the metal layer, the support layer should preferably be a good electrical insulator. In an example embodiment, the metal layer may be fabricated from nickel and the support layer may be fabricated from a hydrocarbon/ceramic laminate. The thermal expansion coefficient of nickel is approximately 13.1 µm/m-° C. Examples of well-thermally-matched support materials are Rogers 4350 and Rogers 3210 (Rogers Corporation, Rogers, Conn.) both of which are hydrocarbon/ceramic laminate materials that are used in the manufacture of certain printed circuit boards.

Other materials ideal for the supporting layer due to their high temperature resistance, stiffness and expansion coefficients are glasses and ceramics such as, but not limited to, Schott P-PK53 Glass (CTE—13.3 µm/m-° C.) and Anderman Ceramics EZY 94 Zirconia, 94%, Yttria-Stabilized (CTE—10.3 µm/m-° C.).

In an illustrative embodiment, the support layer 30 is preferably an annular rectangular frame as illustrated in FIG. 1B. This frame 30 may optionally have metal pads formed on one or more of its surfaces to facilitate certain types of attachment to the metal layer and to other elements of the FAIMS system. A variation of the structure illustrated in FIG. 1B is to additionally attach a second, nominally identical frame to the other side of the metal layer, to improve the dimensional stability of the ion channels under temperature variation.

Figure 2:
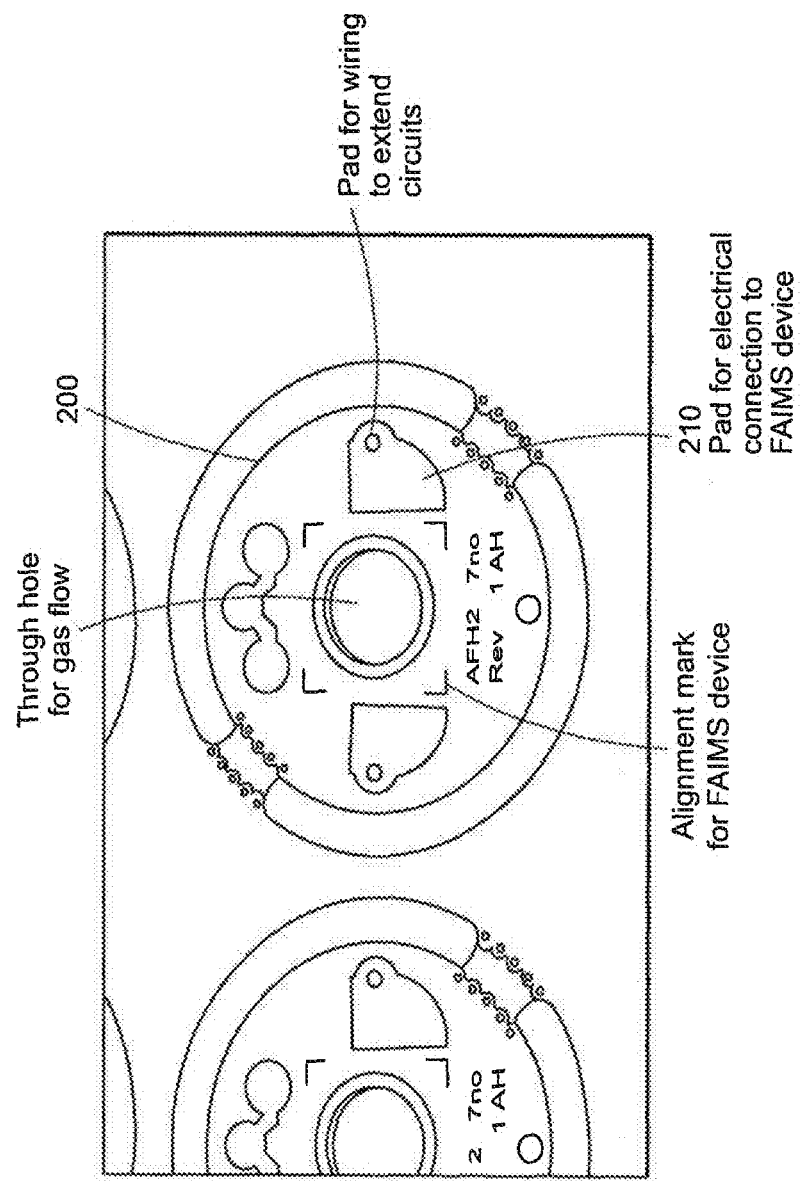
FIG. 2 depicts a design for a printed circuit board for interfacing the FAIMS filter to other portions of a FAIMS system in accordance with a certain illustrated embodiment.

In accordance with another illustrative embodiment, the support layer (frame) may be a structure that also performs other functions, such as providing an electrical interconnection interface to other parts of the FAIMS system. With reference to FIG. 2, and as an example, the metal layer could be directly bonded to a printed circuit board 200, which incorporates pads 210 to allow wires to be connected to the FAIMS driver circuits. Such a printed circuit board 200 could be based on either plastics, ceramics or a composite of both. If the printed circuit board is ceramic then it may be fabricated using either thick or thin film metallisation techniques well known to one skilled in the art. Electrical interconnection between the circuit board 200 and the metal FAIMS electrodes could be made by direct soldering of the metal layer to the circuit board before removal of the metal tabs, by gold thermocompression bonding of the metal layer to the circuit board or by solder, thermocompression or thermosonic attachment of wires between the metal layer and the circuit board.

Figure 3A:
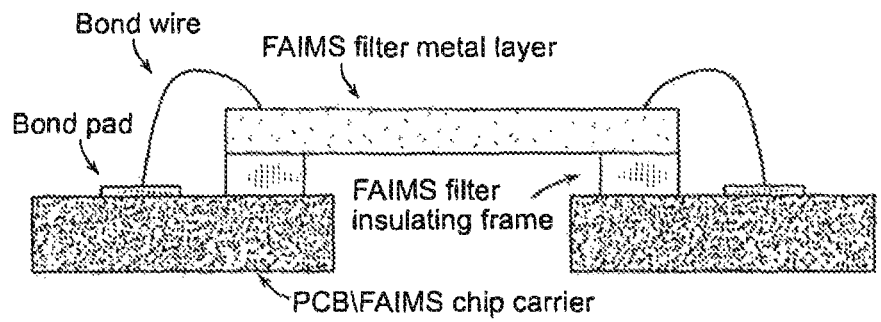
FIGS. 3A-3E depict various illustrative embodiments of the insulating support layer and associated methods for making electrical connections to FAIMS drive circuits.
Figure 3B:
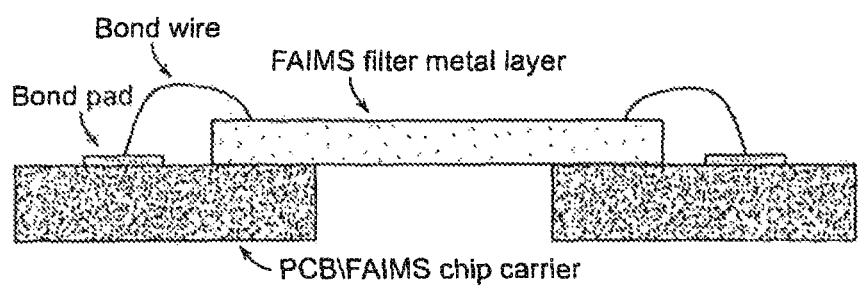
Figure 3C:
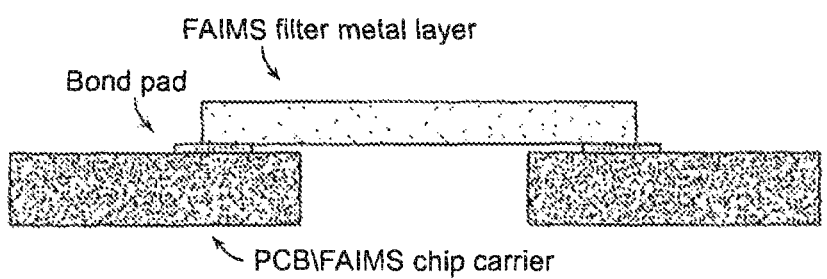
Figure 3D:
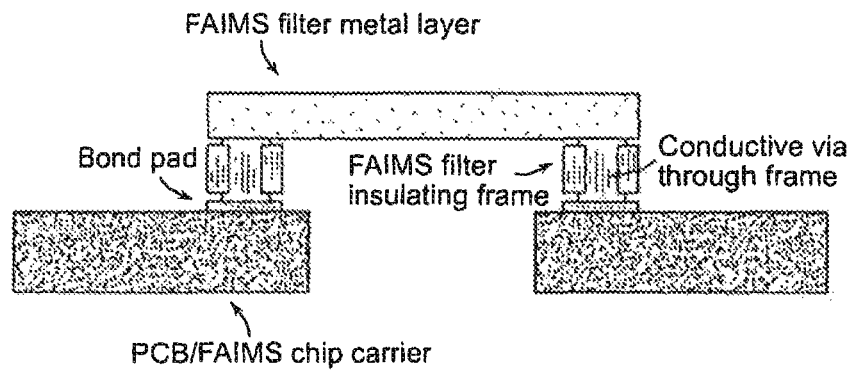
Figure 3E:
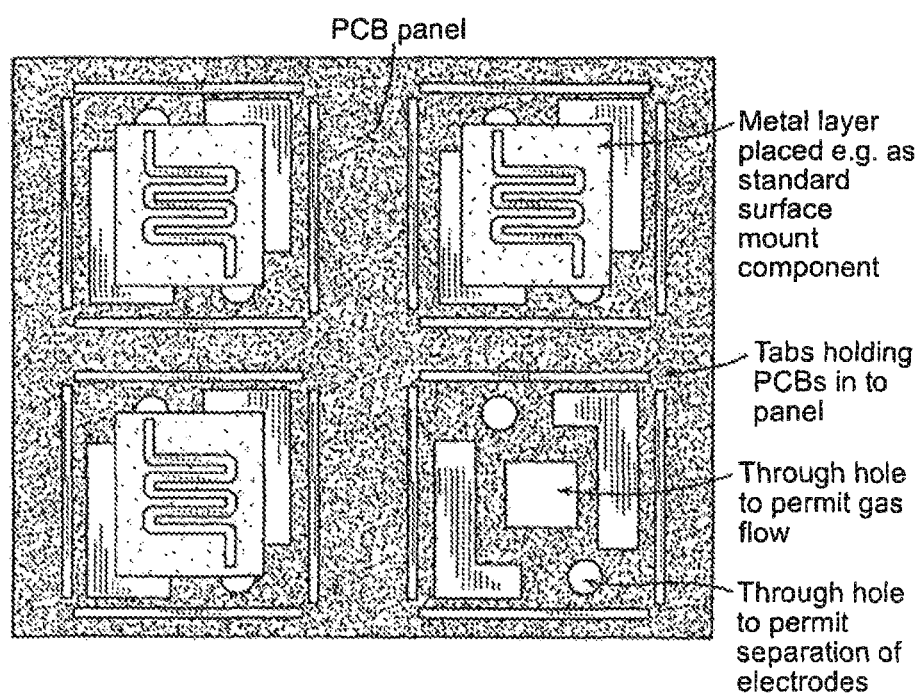

For instance, various options for electrical and mechanical attachment are depicted in the illustrated embodiments of FIGS. 3A-3E. In particular, FIGS. 3A-3E illustrate examples of implementations for the insulating support layer (frame) and associated methods for making electrical connections to the FAIMS drive circuits 200. For instance, FIG. 3A depicts a two-layer FAIMS device with insulating frame bonded on to PCB/FAIMS chip carrier, with electrical connection made using wires. FIG. 3B depicts a single-layer FAIMS device bonded directly on to PCB/FAIMS chip carrier with electrical connections made using wires. FIG. 3C depicts a single-layer FAIMS device bonded directly on to electrical contact pads on the PCB/FAIMS chip carrier—for example using solder, conductive adhesive or thermocompression bonding. FIG. 3D depicts a two-layer FAIMS device with insulating frame containing conductive through vias, with direct electrical connections being made between FAIMS device, frame and PCB/FAIMS chip carrier. And FIG. 3E depicts an example of how devices can be readily assembled in large numbers using surface-mount PCB assembly techniques to automate attachment and electrical interconnection, for example using solder paste and a reflow oven to attach the metal layer to the PCB layer.

It is to be appreciated the support layer for the FAIMS device may also incorporate other electronic components. For example, it may be advantageous to add a compensating capacitor to the support layer, electrically connected so as to add to the capacitative load seen by the FAIMS driver circuit when driving the FAIMS device. Such a capacitor could be fitted, for example, to ensure that the driver circuit is exposed to the same capacitance when driving FAIMS devices of different intrinsic capacitances. The second compensating capacitor would be chosen with reference to the capacitance of the FAIMS device to bring the total load up to a standard reference level. This arrangement ensures that the performance of the FAIMS drivers was constant across different FAIMS device designs.

Illustrative Attachment Methods for the Metal Layer and Support Layer

It is to be appreciated the method used to attach the metal layer containing the ion channels and the insulating support layer is preferably able to withstand process and operating temperatures for the FAIMS device, form a rigid and durable mechanical connection, maintain electrical isolation across the ion channels and avoid introducing chemical contaminants in to the gas flowing through the FAIMS device. For instance, various suitable attachment methods are discussed below.

For instance, and with reference to Table 1, a chemically inert insulating epoxy may be used to attach the two layers, such as use of epoxy which does not require any metal pads to be formed on the support layer.

TABLE 1

| -Composition Of Epoxy Used For Device Construction- | | |
|---|---|---|
| Ingredient | CAS no | % age |
| Epichlorhydrin/Bisphenol A Epoxy Resin (MW, 700) | 25068-38-6 | >90% |
| Glycidyl Ether | 2461-15-6 | <10% |
| Amorphous silica | 60842-32-2 | 0-40% |

Alternative to epoxy, if the support layer has been formed with appropriately positioned metal pads on the attachment surface, the metal layer may be soldered to the support. It is noted to maintain electrical isolation, the metal pads are patterned so as not to form a conducting bridge between the FAIMS electrodes. It is to be appreciated the type and method of application and reflow of the solder can be chosen according to the materials used to form the metal layer and the pads on the support layer. One method of such attachment includes the usage of pre-tinning pads on a support frame with lead-tin solder and re-flowing using a hot-plate to bond to a nickel metal layer containing the ion channels. However, other processes using solid solder and solder pastes are well known and could be used to perform this attach.

It is noted if there is a need to produce FAIMS devices on a large scale, it may be advantageous to form many support frames on a PCB panel, held into the panel using small tabs. The standard techniques used for surface mount PCB assembly could then be used to apply solder paste to defined areas of the support-frame PCB, place the metal FAIMS devices either manually or with an automatic pick and place machine, then re-flow the solder paste in a standard re-flow oven. After soldering, the individual bonded devices are removed from the panel by cutting the PCB tabs, prior to separation of the metal electrodes (described below). With reference to FIG. 3E, depicted is an example structure that could be assembled in this manner. Additionally, a third method for attachment to a support frame with appropriate patterned metal pads is to use gold thermocompression bonding.

With regards to yet another alternative process, multiple metal devices can be produced on a sheet (e.g. attached to the sheet using tabs) and the whole sheet bonded to a matching sheet of Frames. In this embodiment the isolation of the two halves of the FAIMS filter can be accomplished with the same process that separates the devices (e.g. a standard semiconductor process of dicing using a dicing saw). And in yet another alternative and packaging process, the metal structure can be encapsulated in a high temperature epoxy producing a package similar to standard dual-in-line (DIL) chip packages.

Illustrative Methods for Removal of Tabs on the Metal Layer (Electrical Isolation)

After attachment of the metal layer to the insulating support or frame, the tabs holding the metal layer in one piece are removed to electrically isolate the two or more electrodes of the structure. This can be achieved by any of a number of methods including (but not limited to); use of a dicing saw, laser ablation, selective chemical etching, mechanical clipping and mechanical abrasion and the like.

Variable Effective Active Area FAIMS Device

Under many circumstances it is desirable to change the active area of the FAIMS chip, for example to trade off resolution/transmission. In this case a further refinement on this invention is to incorporate an opening proximate to the chip (typically less than 1 mm). By changing the dimensions of this opening air is caused to pass through either all of the chip or only part of the chip. This allows the active area of the chip to change quickly and easily without any significant change to the RF waveform. For instance, the opening could be (but not limited to) a circle, square or rectangle; these openings could be either replaced or held in some form of rotary assembly to allow easy and repeatable switching of apertures.

In another illustrative embodiment, a single aperture assembly such as a camera type iris or single adjustable plate could be used. In the case of the plate, this could be mounted in a micrometer and create a variable diameter rectangle over the open area of the chip. It is noted in previous embodiments the openings could be either up or downstream of the chip or on both sides simultaneously.

Heat Sinking of RF Transistor

It is to be appreciated that the capacitance of the RF stage is a critical parameter in determining system performance; however, dissipating the heat from the RF switching transistor to a metallic heat sink, which must be earthed for EMC and safety reasons, can be problematic. Insulating materials with high thermal conductivities such as, but not limited to, aluminum nitride (AlN) and beryllium oxide (BeO) are advantageous in this respect.

In one illustrative embodiment, an RF drive transistor having an electrically active heat sink tab is thermally connected to, but electrically insulated from, an RF return or chassis ground via an electrically insulating spacer (e.g. AlN, metal/AlN/metal). The spacer is made thick enough (e.g. 0.2-5 mm) to sufficiently minimize the capacitive coupling between the transistor terminal and ground. In another illustrative embodiment, an RF drive transistor having a heat sink tab that is electrically connected to RF return ground is thermally connected to chassis ground via an electrically insulating spacer (e.g. AlN), which prevents direct electrical connection between the grounds.

Asymmetric Waveform

It is to be understood, the asymmetric waveform generator circuitry typically must be located at a distance from the FAIMS filter assembly due to practical constraints, which may include: operation of the FAIMS filter assembly at very high temperatures does not produce a conducive environment for the high power waveform generator circuitry; heat generated by waveform generator circuitry necessitates external cooling, and not enough room in the vicinity of the filter assembly to accommodate the waveform generator circuitry. This physical separation results in some technical difficulties. It is to be appreciated that it is difficult to transmit an asymmetric waveform any appreciable distance without adversely affecting the waveform properties. The waveform shape will be altered to reduce the effective duty cycle, for example due to broadening of the high voltage pulse or ringing during the low voltage trough. Waveform voltages (and hence electric fields produced) will decrease with increasing transmission distance.

Secondly, the transmission path itself can load the asymmetric waveform generator circuitry so as to degrade the quality of the waveform generated in the first place or even prevent the circuitry from functioning altogether. This is especially the scenario where the transmission path appears to the driver circuit as a large reactive (i.e. capacitive or inductive) load. Additionally, it is preferable the transmission path be physically robust to prevent changes in the transmitted waveform due mechanical movement. As high voltages are typically involved, sufficient isolation of the high voltage components is provided to meet all safety regulations.

Illustrative Embodiments of the Invention

Preferably, the RF feeder structure is composed of a coaxial transmission line formed from a hollow rigid conductor and wire running through the space within. The rigid conductor is enclosed in a rigid plastic shell surrounded by an outer metal shell, which is grounded for safety reasons. The hollow rigid conductor is, for example, made of copper. The wire is preferably of the insulated type and has a diameter as small as practical to maximize the surrounding air gap.

Air is preferably used as the dielectric material for the transmission line since air minimizes the diameter of the coaxial structure. The hollow rigid conductor may, for example, have an inner diameter ranging from 5 mm to 15 mm. Spacers are preferably used to hold the wire along the centreline of the hollow rigid conductor. The wire is held along the axis of the rigid conductor by two electrically insulating spacers, preferably one at either end. A coaxial transmission line is preferably used for each of the two channels of the filter electrode. The hollow rigid conductor may held at a non-zero voltage so as to deliver a bias voltage to the FAIMS filter assembly. This form of transmission line is ultra-stable and presents relatively low parasitic reactance's to the waveform generator circuit.

Asymmetric Waveform Generator Circuit

It is to be appreciated that one method of generating an asymmetric waveform is to employ a class E amplifier circuit that has been de-tuned so as to produce a heavily distorted sinusoid. Distortion can be achieved by driving at a suitable frequency and duty cycle so as to produce a peak duration-to-trough duration waveform of approximately 35 percent or less. Use of a transformer between the drain of a FET driver (e.g. a MOSFET driver) and power supply rail rather than an inductor can yield a voltage gain roughly in proportion to the turns ratio. A transformer can also be used to generate two symmetric waveforms that can be applied to the opposite sides of the FAIMS filter to generate an identically shaped electric field waveform with twice the field intensity. An ISM (Industrial Scientific Medical) band frequency may be used as the fundamental frequency to facilitate EMI compliance; however, harmonics will extend into the sidebands.

Method of Tuning

The asymmetric waveform generator circuitry is preferably tuned for optimal operation. It is noted an ideal waveform shape is difficult to determine. Generally speaking, it is desirable to maximize the peak voltage while maintaining a duty cycle less than about 35 percent. Because the tuning process can be complex and time consuming, the following method of tuning has been developed.

In accordance with an illustrative embodiment, tuning is achieved by changing the values of two capacitances in the circuit, each capacitance being composed of one or more discrete capacitors in parallel:

(1) One parallel to the filter chip, and
(2) One across the drain and source terminals of the FET.

The first capacitor value is preferably changed to adjust the general waveform shape and the second capacitor value is changed to increase or decrease the peak voltage and peak width. Fixed value capacitors are preferably employed; however, variable or other specialized type (e.g. laser trimmable) capacitors may alternatively be used. The FET is replaced and the process repeated if power requirements are not met.

Figure 4A:
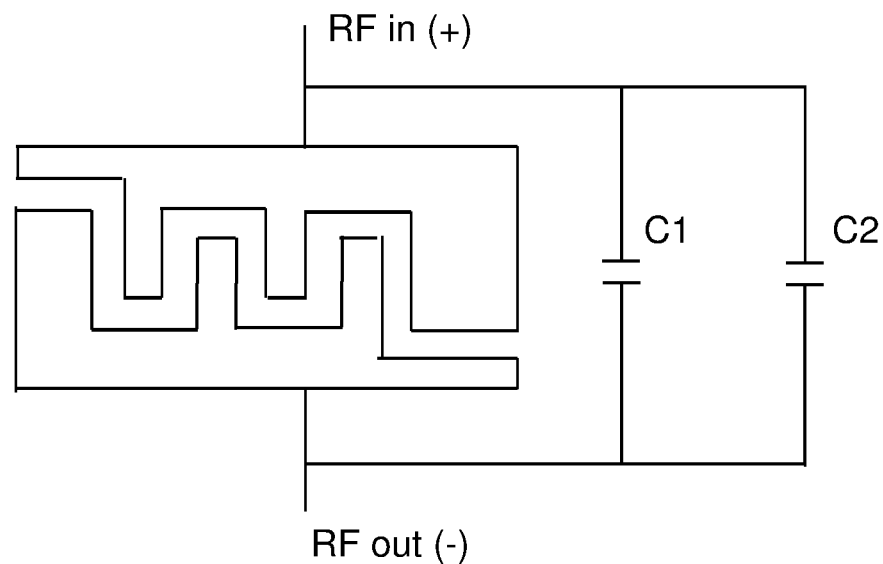
FIG. 4A depicts a metal electrode layer separated into two portions with two discrete capacitors connected across the two portions of the electrode layer, in accordance with certain illustrated embodiments.

FIG. 4A depicts a metal electrode layer separated into two portions with two discrete capacitors connected across the two portions of the electrode layer, in accordance with certain illustrated embodiments.

Figure 4B:
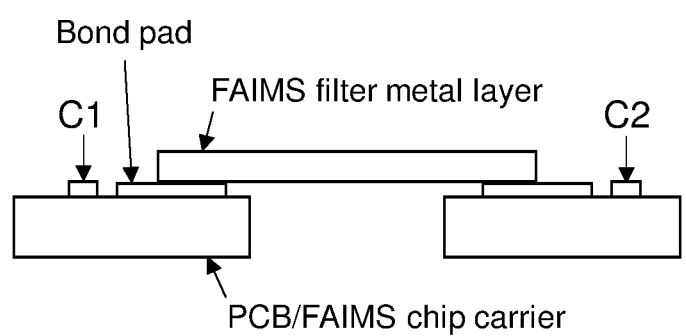
FIG. 4B depicts the FAIMS filter metal electrode layer bonded directly onto electrical contact pads on the PCB/FAIMS chip carrier, as shown in FIG. 3C, with the discrete capacitors of FIG. 4A, in accordance with certain illustrated embodiments.

FIG. 4B depicts the FAIMS filter metal electrode layer bonded directly onto electrical contact pads on the PCB/FAIMS chip carrier, as shown in FIG. 3C, with the discrete capacitors of FIG. 4A, in accordance with certain illustrated embodiments.

It is to be appreciated the above presents a description of a best mode contemplated for carrying out the present invention, and of the manner and process of making and using them, in such full, clear, concise, and exact terms as to enable any person skilled in the art to which it pertains to make and use these devices and methods. The present invention is, however, susceptible to modifications and alternative method steps from those discussed above that are fully equivalent. Consequently, the present invention is not limited to the particular embodiments disclosed. On the contrary, the present invention encompasses all modifications and alternative constructions and methods coming within the spirit and scope of the present invention. Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function, it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. An ion filter, comprising:
at least one metal electrode layer, the at least one metal electrode layer having a serpentine trench which defines a plurality of ion channels and which extends through the at least one metal electrode layer to separate the at least one metal electrode layer into two halves; and
at least one support layer affixed adjacent to the two halves of the at least one metal electrode layer;
wherein the at least one support layer is annular with a central aperture formed therein configured to permit gas to flow therethrough; and
wherein the at least one support layer is positioned on edges of the at least one metal electrode layer with at least part of the at least one support layer over ends of the serpentine trench to maintain the two halves of the at least one metal electrode layer in fixed relative positions to one another.

2. The ion filter as recited in claim 1, wherein the at least one support layer is configured as an electronic circuit carrier.

3. The ion filter as recited in claim 2, wherein the at least one support layer includes at least one capacitance in parallel with the at least one metal electrode layer.

4. The ion filter as recited in claim 3, wherein the at least one capacitance is at least partially formed by one or more discrete capacitors.

5. The ion filter as recited in claim 1, wherein the at least one support layer is configured to provide electrical interconnection between the two halves of the at least one metal electrode layer and ion filter drive electronics.

6. The ion filter as recited in claim 5, wherein the electrical interconnection is provided by wire bonding the two halves of the at least one metal electrode layer and the at least one support layer.

7. The ion filter as recited in claim 5, wherein the electrical interconnection is provided by soldering the two halves of the at least one metal electrode layer and the at least one support layer.

8. The ion filter as recited in claim 1, wherein the at least one support layer comprises ceramic material.

9. The ion filter as recited in claim 1, wherein the at least one support layer comprises a composite containing one or more of ceramic, glass and hydrocarbon materials.

10. The ion filter as recited in claim 1, wherein the at least one support layer comprises glass.

11. The ion filter as recited in claim 1, wherein the at least one support layer provides conductive pads for mechanical and electrical connection to the two halves of the at least one metal electrode layer.

12. The ion filter as recited in claim 11, wherein the at least one support layer is configured to provide electrical interconnection between the two halves of the at least one metal electrode layer and ion filter drive electronics.

13. The ion filter as recited in claim 1, wherein the at least one support layer has an expansion co-efficient approximately equal to an expansion co-efficient of the at least one metal electrode layer.

14. The ion filter as recited in claim 1, wherein the at least one metal electrode layer is separated into the two halves during a fabrication process by removing at least one separating structure that maintains the two halves in a fixed mechanical separation.

15. The ion filter as recited in claim 14, wherein the at least one separating structure is removed after the at least one support layer is affixed to the two halves.

16. A method for fabricating ion filter devices, the method comprising the following steps:
fabricating an array of support structures on a sheet;
fabricating a plurality of electrode structures by forming a plurality of electrode layers each having a serpentine trench which defines a plurality of ion channels, wherein each serpentine trench extends proximal to edges of each corresponding electrode layer to separate the corresponding electrode layer into two halves joined by a pair of separating structures for maintaining a fixed mechanical separation between the two halves;
attaching said fabricated plurality of electrode structures to said sheet having said fabricated array of support structures with each electrode structure in said plurality of electrode structures being attached to a respective support structure, wherein each respective support structure is a frame on edges of each respective electrode structure and said pair of separating structures;
removing, after said attaching step, said pair of separating structures for each said electrode structure to provide electrical isolation between said two halves; and
separating each electrode structure and its respective attached support structure to provide individual ion filter devices.

17. The method for fabricating ion filter devices as recited in claim 16, wherein said fabricating said array of support structures comprises fabricating said array of support structures as a printed circuit board panel.

18. The method for fabricating ion filter devices as recited in claim 16, wherein said attaching is selected from soldering, brazing, welding, thermocompression bonding and adhesive bonding.

19. The method for fabricating ion filter devices as recited in claim 16, further comprising joining the plurality of electrode structures together in a sheet prior to the attaching step.

20. An ion filter, comprising:
at least one metal electrode layer, the at least one metal electrode layer having at least one ion channel separating the at least one metal electrode layer into two or more electrodes; and
at least one support layer affixed adjacent to the two or more electrodes of the at least one metal electrode layer;
wherein the at least one support layer is annular with a central aperture formed therein configured to permit gas to flow therethrough;
wherein the at least one support layer is positioned on the at least one metal electrode layer with at least part of the at least one support layer over at least part of the at least one ion channel to maintain the two or more electrodes of the at least one metal electrode layer in fixed relative positions to one another;
wherein the at least one support layer is configured as an electronic circuit carrier;
wherein the at least one support layer includes at least one capacitance in parallel with the at least one metal electrode layer; and
wherein the at least one capacitance is at least partially formed by one or more discrete capacitors.

* * * * *